(12) United States Patent
Chang

(10) Patent No.: US 7,951,386 B2
(45) Date of Patent: *May 31, 2011

(54) EHRLICHIA CANIS GENES AND VACCINES

(75) Inventor: Yung-Fu Chang, Ithaca, NY (US)

(73) Assignee: Cornell University, Ithaca, NY (US)

( * ) Notice: Subject to any disclaimer, the term of this patent is extended or adjusted under 35 U.S.C. 154(b) by 112 days.

This patent is subject to a terminal disclaimer.

(21) Appl. No.: 12/017,144

(22) Filed: Jan. 21, 2008

(65) Prior Publication Data

US 2008/0220007 A1 Sep. 11, 2008

Related U.S. Application Data

(60) Division of application No. 10/004,494, filed on Nov. 2, 2001, now Pat. No. 7,335,754, which is a continuation-in-part of application No. 09/358,322, filed on Jul. 21, 1999, now abandoned.

(51) Int. Cl.
*C12N 15/00* (2006.01)
*C07H 21/02* (2006.01)
*A61K 45/00* (2006.01)
*A61K 49/00* (2006.01)
*A61K 48/00* (2006.01)

(52) U.S. Cl. .................. 424/278.1; 424/9.2; 435/320.1; 536/23.1; 514/44 R

(58) Field of Classification Search .................. 424/9.2, 424/278.1; 435/320.1; 536/23.1
See application file for complete search history.

(56) References Cited

U.S. PATENT DOCUMENTS

| | | | |
|---|---|---|---|
| 5,192,679 A | 3/1993 | Dawson et al. | |
| 5,401,656 A | 3/1995 | Dawson | |
| 5,413,931 A | 5/1995 | Dawson | |
| 6,043,085 A | 3/2000 | Yu et al. | |
| 6,593,114 B1 * | 7/2003 | Kunsch et al. | 435/91.41 |
| 7,335,754 B2 * | 2/2008 | Chang | 536/23.1 |

FOREIGN PATENT DOCUMENTS

| | | |
|---|---|---|
| WO | WO-9816554 | 4/1998 |
| WO | WO9816554 A | 4/1998 |
| WO | WO-9842743 | 10/1998 |
| WO | WO-9842743 A | 10/1998 |
| WO | WO-9913720 | 3/1999 |
| WO | WO-9913720 A | 3/1999 |
| WO | WO-0032745 A | 6/2000 |
| WO | WO-0107625 A2 | 2/2001 |

OTHER PUBLICATIONS

Ellis R, New Technologies for Making Vaccines, 1998, pp. 568-575.*
Maender et al., Dermatological Therapy, 2004, vol. 17, pp. 499-504.*
Boslego et al., 1998, Vaccines, Chapter 17, pp. 211-223.*
Drs. Foster and Smith Educational Staff, Ehrlichiosis in Dogs, 2 page print out.*
Donnolly et al., 2005, J. Immunology, vol. 175, pp. 633-639.*
Sasaki et al., 2003, Methods, vol. 31, pp. 243-254.*
2003, Editorial, Methods, vol. 31, pp. 183-192.*
Pejawar-Gaddy et al., 2008, Critical Rev. in Oncology/Hematology, vol. 67, pp. 93-102.*
Hokey et al., 2006, Spring Semin. Immun., vol. 28, pp. 267-279.*
Centers for Disease Control (CDC), Tickborne Rickettsial Diseases, 2-page printout).*
Unver et al., 2001, J. Clin. Micro., vol. 39(8), pp. 2788-2793.*
Chen et al., 1996, Am. J. Med. Hyg., vol. 54(4), pp. 405-412.*
Dumler et al., 2001, Int. J. Systematic and Evolutionary Microb., vol. 51, pp. 2145-2165.*
Altschul, S.F. et al., 1990, Basic local alignment search tool, J. Mol, Biol 215: 403-410.
Altschul, S. et al., 2001, Results of Blast, http: //www.ncbi.nlm.nih.gov/blast/Blast.cgi, Sep. 14, 2001, 40 pages.
Appel, M.J. et al., 1993, Experimental Lyme Disease in Dogs Produces Arthritis and Persistent Infection, Journal of Infectious Diseases 167: 651-654.
Betsou, F. et al., 1995, Cloning and sequence of the *Bordetella bronchiseptica* adenylate cyclase-hemolysin-encoding gene: comparison with the *Bordetella* pertussis gene, Gene 162: 165-166.
Bohm et al., 1996, DNA vector constructs that prime hepatitis B surface antigen-specific cytotoxic T lymphocyte and antibody responses in mice after intramuscular injection, J. Immunol. Methods 193: 29-40.
Breitschwerdt, E.B. et al., 1998, Doxycycline hyclate treatment of experimental canine *Ehrlichiosis* followed by challenge inoculation with two *Ehrlichia canis* strains, Antimicrobial Agents and Chemotherapy 42(2): 362-368.
Chang, W.L. et al., 1996, Specific Amplification of *Ehrlichia platys* DNA from blood specimens by two-step PCR. J. Clin. Micro.: 34 (12): 3142-3146.
Chang, Y.F. et al., 1987, Identification and characterization of the *Pasteurella haemolytica* Leukotoxin, Infect. Immun. 55: 2348-2354.
Chang, Y.F. et al., 1989a, Secretion of the *Pasteurella* eukotoxin by *E. coli*, FEMS Microbiology Let. 60: 169-174.
Chang, Y.F. et al., 1989b, Cloning and Characterization of a hemolysin gene from *Actinobacillus* (*Haemophilus*) *pleuropneumoniae*, DNA 8(9): 635-647.
Chang, Y.F. et al., 1993a, Molecular characterization of a leukotoxin gene from a *Pasteurella haemolytica*-like organism, encoding a new member of RTX family, Infect. Immun. 61: 2089-2095.
Chang, Y.F. et al., 1993b, Molecular analysis of the *Actinobacillus pleuropneumoniae* RTX toxin-III gene cluster, DNA and Cell Biol. 12: 351-362.
Chang, Y.F. et al., 1993c, Expression and secretion of outer surface protein (OspA) of *Borrelia burgdorferi* from *E. coli*, FEMS Microbiol. Lett. 109: 297-302.
Chang, Y.F. et al., 1995, Recombinant OspA protects dogs against infection and disease caused by *Borrelia burgdorferi*, Infect. Immun. 63: 3543-3549.

(Continued)

*Primary Examiner* — Peter Paras, Jr.
*Assistant Examiner* — David Montanari
(74) *Attorney, Agent, or Firm* — Marijama Muldoon Blasiak & Sullivan LLP

(57) ABSTRACT

This invention provides the sequence of 5,299 nucleotides from the *E. canis* genome. There are four proteins, ProA, ProB, MmpA, and a cytochrome oxidase homolog, as well as a partial lipoprotein signal peptidase homolog at the carboxy terminus, coded for in this cloned fragment. The antigenic properties of these proteins allow them to be used to create a vaccine. An embodiment of this invention includes the creation of a DNA vaccine, a recombinant vaccine, and a T cell epitope vaccine. Another embodiment of this invention includes the use of serological diagnosis techniques.

15 Claims, 1 Drawing Sheet

OTHER PUBLICATIONS

Figure 1:
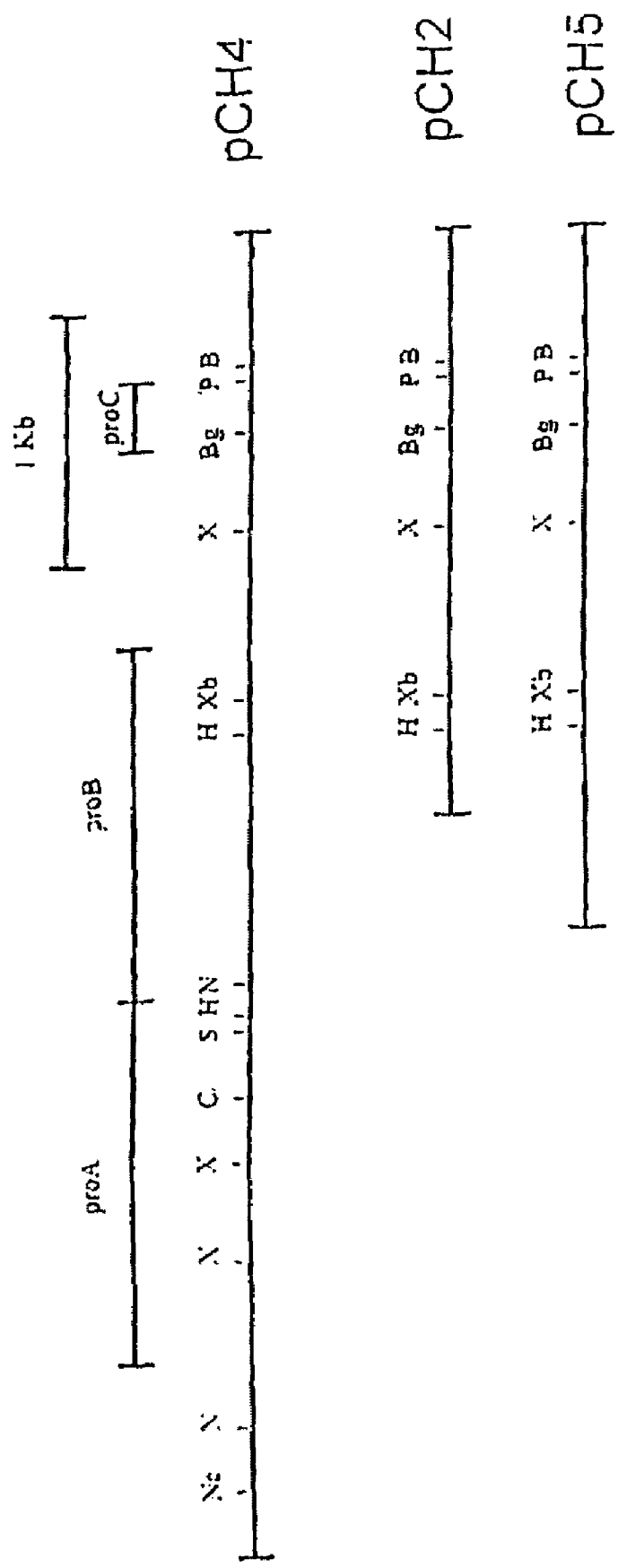

Chang, Y. F. et al., 1998, Detection of human granulocytic ehrlichiosis agent and *Borrelia burgdorferi* in ticks by polymerase chain reaction, J. Vet. Diagn Invest. 10: 56-59.

Chang, Y.F. et al., 1998, Experimental infection of the human granulocytic ehrlichiosis agent in horses, Veterinary Para. 78: 137-145.

Chen et al., 1994, Identification of the antigenic constituents of *Ehrlichia chaffeensis*, Am. J. Tropic. Med. Hyg. 50: 52-58.

Cotter, P.A. and Miller, J.F., 1994, BvgAS-mediated signal transduction: analysis of phase-locked regulatory mutants of *Bordetella bronchiseptica* in a rabbit model, Infect. Immun. 62: 3381-3390.

Database EMPRO1, Anderson, S.G. et al., 1998, The genome of sequence of Rickettsia prowazekii and the origin of mitochondria, 1 page.

Database EMPRO1, Yamane, K. et al., 1997, The 25 degrees region of the *Bacillus subtilis* chromosome determination of the sequence of a 146kb segment and identification of 113 genes, 1 page.

Database NCBI, Accession No. AX077837, Chang, Y.F. Feb. 22, 2001.

Dawson et al., 1991, Serologic diagnosis of human *Ehrlichiosis* using two *Ehrlichia canis* isolates, Journal of Infectious Diseases 163: 564-567.

Degen, et al., 1986, The human tissue plasminogen activator gene, Journal of Biological Chemistry 261(15): 6972-6985.

Donnelly et al., 1993, Targeted delivery of peptide epitopes to class I major histocompatibility molecules by a modified Pseudomonas exotoxin, Proc. Natl. Acad. Sci. USA 90: 3530-3534.

Dumler et al., 1992, Cell-mediated immune responses of adults to vaccination, challenge with Rickettsia rickettsii, or both, Am. J. Trop. Med. Hyg 46(2): 105-115.

EMBL, Heidelberg, Germany, I40883, Aug. 16, 1996, Abstract.

Fayolle et al., 1996, In vivo induction of CTL responses by recombinant adenylate cyclase of *Bordetella pertussis* carrying viral CD8+ T cell epitopes, J. Immun. 156: 4697-4706.

Freiberg, C. et al., 1997, Molecular basis of symbiosis between Rhizobum and legumes, Nature 387: 384-401.

Fynan et al., 1993, DNA vaccines: protective immunizations by parenteral, mucosal and gene-gun inoculations, Proc. Natl. Acad. Sci. USA 90: 11478-11482.

Gish, W. et al., 1993, Identification of protein coding regions by database similarity, Natural Genetics 13: 266-272.

Goldman, L.A. et al., 1996, Modifications of vectors pEF-BOS, pcDNA1 and pcDNA3 result in improved convenience and expression, BioTechniques 21: 1013-1015.

Guermonprez, P.D. et al., 1999, Direct delivery of the *Bordetella pertussis* adenylate cyclase toxin to the MHC class I antigen presentation pathway, J. Immunol. 162: 1910-1916.

Gupta, R.K. and Siber, G.R., 1995, Adjuvants for human vaccines-current status, problems and future prospects, Vaccine 13(14): 1263-1276.

Harrus, et al., 1998, Amplification of Ehrlichial DNA from dogs 34 months after infection with *Ehrlichia canis*, Journal of Clinical Microbiology 36(1): 73-76.

Keysary et al., 1996, The first isolation, in vitro propagation, and genetic characterization of *Ehrlichia canis* in Israel, Veterinary Parasitology 62: 331-340.

Klinman, D.M. et al., 1997, CpG motifs as immune adjuvants, Vaccine 17: 19-25.

Launois et al., 1994, T-cell epitope mapping of the major secreted myobacterial antigen Ag85A in tuberculosis and leprosy, Infection and Immunity 62(9): 3679-3687.

Lee, B. and Horwitz, M.A. 1999, T-cell epitope mapping of the three most abundant extracellular proteins of Myobacterium turberculosis in outbred guinea pigs, Infection and Immunity 67(5): 2665-2670.

Lewis et al., 1994, Sequence, organization, and evolution of the A+T region of *Drosophila* Melanogaster mitochondrial DNA, Mol. Biol. Evol. 11: 523-538.

McBride J. et al., 2000, Immunodiagnosis of *Ehrlichia canis* infection with recombinant proteins J. Clin. Microbiology 39 (1): 315-322.

Nyika, A. et al., 1998, A DNA vaccine protects mice against the rickettsial agent Cowdria ruminantium, Parasite Immunol. 20: 111-119.

Ogaswara et al., 1992, A strategy for making synthetic peptide vaccines. Proc. Natl. Acad. Sci. USA 89 (Oct): 8995-8999.

Palaniappan R.U.M., et al., 2002, Cloning and molecular characterization of an immunogenic LigA protein of *Leptospira interrogans*, Infect. Immun. 70(11): 5924-5930.

Rikihisa et al., 1992, Analyses of *Ehrlichia canis* and a canine granulocytic *Ehrlichia* infection, Journal of Clinical Microbiology 30(1): 143-148.

Robinson, H.L., 1997, Nucleic acid vaccines: an overview, Vaccine 15(8): 785-787.

Sebo, P.C. et al., 1995, Cell-invasive activity of epitope-tagged adenylate cyclase of *Bordetella pertussis* allows in vitro presentation of a foreign epitope to CD8+ cytotoxic T cells, Infect. Immun. 63: 3851-3857.

Springer, A. L. et al., 1996, Characterization and Nucleotide Sequence of pqqE and pqqF in Methlobacterium extorguens AM1, J. Bacteriology 178 (7); 2154-2157.

Stewart, G.S. et al., 1986, pHG165: A pBR322 copy number derivation of pUC8 for cloning and expression, Plasmid 15: 172-186.

Storey, J.R. et al., 1998, Molecular cloning and sequencing of three granulocytic *Ehrlichia* genes encoding high-molecular-weight immunoreactive proteins, Infection and Immunity 66(4): 1356-1363.

Teng C.-H. et al., 2003, Cloning and characterization of an *Ehrlichia canis* gene encoding a protein localized to the morula membrane, Infect. Immun. 71(4): 2218-2225.

Teng C.-H. et al., 2003, Cloning and characterization of putative zinc protease genes of *Ehrlichia canis*, DNA Sequence 14(2): 109-121.

Uetsuki et al., 1989, Isolation and characterization of the human chromosomal gene from polypeptide chain elongation factor-1α, Journal of Biological Chemistry 264(10): 5791-5798.

Verma et al., 1997, Gene therapy-promises, problems and prospects, Nature 389: 239-242.

Vical Inc. Two page printout from www.vical.com web pages: p. 1, Company Info, p. 2, Research.

Waghela, S.D. et al., 1991, A cloned DNA probe identified Cowdria ruminantium in Amblyomma variegatum ticks, J. Clin. Microbiol. 29 (11): 2571-2577.

Wen et al., 1997, Comparison of nested PCR with immunofluorescent-antibody assay for detection of *Ehrlichia canis* infection in dogs treated with doxycycline, J. Clin. Microbiol. 35(7): 1852-1855.

White, A.P. et al., 1999, High efficiency gene replacement in *Salmonella enteritidis*: chimeric fimbrins containing a T-cell epitope from Leishmania major, Vaccine 17: 2150-2161.

Yu X-J. et al., 2000, Molecular cloning and characterization of the 120-kilodalton protein gene of *Ehrlichia canis* and application of the recombinant 120-kilodalton protein for serodiagnosis of canine ehrlichiosis J. Clin. Microbiology 38 (1): 369-374.

Yuk, M.H. et al., 1998, The BvgAS virulence control system regulates type III secretion in *Bordetella bronchiseptica*, Mol. Microbiol. 28: 945-959.

Reporting Letter From Brazilian Associate dated Nov. 10, 2010 (redacted) forwarding Ministry of Development, Industry and Foreign Trade, National Institute of Industrial Property, Directorate of Patents—DIRPA, Technical Examination Report dated Sep. 30, 2010, (3 pgs.).

* cited by examiner

EHRLICHIA CANIS GENES AND VACCINES

CROSS-REFERENCE TO RELATED APPLICATIONS

This application is a divisional application of Ser. No. 10/004,494, filed Nov. 2, 2001, now U.S. Pat. No. 7,335,754, issued Feb. 26, 2008, entitled "*EHRLICHIA CANIS* GENES AND VACCINES," which is a continuation-in-part application of, and claims the benefit of, U.S. patent application Ser. No. 09/358,322, filed Jul. 21, 1999, now abandoned entitled "EHRLICHIA CANIS GENES AND VACCINES," now abandoned. The aforementioned patent and application are each incorporated herein by reference in their entireties.

FIELD OF THE INVENTION

The invention pertains to the field of veterinary pathogens. More particularly, the present invention pertains to the sequence of specific genes of the bacterial canine pathogen *Ehrlichia canis* and the application of this technology to the development of a vaccine.

BACKGROUND OF THE INVENTION

The present invention relates to the sequence of genes from the *E. canis* bacterium, and the development of a vaccine against this organism.

*Ehrlichia canis* (*E. canis*) is a small gram-negative, obligately intracytoplasmic rickettsia. This bacteria is the agent which causes canine monocytic ehrlichiosis (CME), a tick-borne disease which predominantly affects dogs. The most common carrier of *E. canis* is the brown dog tick *Rhipicephalus sanguineus*. The disease was described originally in Algeria in 1935. It was subsequently recognized in the United States in 1962, but is now known throughout much of the world. Canine monocytic ehrlichiosis caused much concern during the Vietnam War, when 160 military dogs died from the *E. canis* infection. There is no vaccination currently available against *E. canis*. It is a life threatening disease that continues to be an important health concern for veterinarians and pet owners alike.

Canine monocytic ehrlichiosis is an infectious blood disease. A reduction in cellular blood elements is the primary characteristic of the disease. *E. canis* lives and reproduces in the white blood cells (leukocytes). It eventually affects the entire lymphatic system, and devastates multiple organs. By targeting the white blood cells, these cells die off rapidly. These dead blood cells migrate primarily to the spleen, which enlarges as a result. The bone marrow recognizes the loss of the white blood cells and works to form new, healthy cells. It sends out the cells prematurely, and these immature cells do not work properly. Often, these immature cells mimic those in leukemic patients, so the disease is misdiagnosed as leukemia. Canine monocytic ehrlichiosis may also predispose dogs to various cancers.

There are three stages of canine monocytic ehrlichiosis. The first, acute stage mimics a mild viral infection. During the acute stage, most, if not all, of the damage is reversible and the animal is likely to recover. This is the stage where treatment is the most effective, stressing the need for early detection. Without treatment, however, the animal will progress into a subclinical (second) stage and/or to the chronic (final) stage. When the animal has reached the chronic stage, the bacterial organism has settled within the bone marrow. Many dogs in this stage suffer massive internal hemorrhage, or develop lethal complications such as sudden stroke, heart attack, renal failure, splenic rupture or liver failure.

*E. canis* can be cultured in vitro in a mammalian-derived cell line (DH82). Continued maintenance of these cells is difficult because the cell culture must be supplemented with primary monocytes (white blood cells found in bone marrow) every two weeks. The cultures are very slow growing, and the culture media is expensive.

Data concerning the genes in the *E. canis* genome has concentrated primarily on the 16S rRNA gene. Previous work has sequenced this gene, which is a ubiquitous component of the members of the ehrlichia family, as well as the majority of organisms worldwide. The high sequence homology between this gene throughout the living world and its poor immunogenicity makes it an unsuitable candidate for vaccine development. It is necessary to find other genes within this genome if hope for a vaccine against this deadly disease can ever be realized.

Sequencing of the 16S rRNA gene indicates that *E. canis* is closely related (98.2% homology) to *E. chaffeensis*, the novel etiologic agent of human ehrlichiosis. Western blots of *E. canis* are similar when probed with antisera to *E. canis, E. chaffeensis*, and *E. ewingi* (another cause of human ehrlichiosis) indicating a close antigenic relationship between these three species (Chen et al., 1994).

The indirect fluorescent antibody test (IFA) has been developed for detecting canine monocytic ehrlichiosis. IFA detects the presence of antibodies against the invading organism in a dog's blood. Unfortunately, this test is not always accurate. Sometimes, dogs will test negative in the acute phase because their immune system is delayed in forming antibodies. Another false negative may occur if there is a low titer in the chronic stage. An additional drawback of this test is the cross-reactivity found. The anti *E. canis* polyclonal antibody positively reacts with *E. chaffeensis*, undermining the specificity of the test. An alternative test, the Giesma smear, has been used to locate the actual organism in a dog's blood. Unfortunately, despite appropriate staining techniques and intensive film examination, the organisms frequently can not be located. The fallibility of these tests makes it essential to provide better diagnostic tools for this disease.

Due to difficulties in the detection of a tick bite, early diagnosis of infection, the suppression of host defenses and the nature of persistent infection of the disease, an effective vaccine against *E. canis* is urgently needed for dogs.

SUMMARY OF THE INVENTION

This invention discloses novel sequence data for *E. canis* genes. Specifically, a clone has been identified and sequenced. Four proteins termed ProA, ProB, mmpA (for morula membrane protein, which is an ORF), and a cytochrome oxidase homolog, have been identified within this clone. In addition, a partial gene encoding a lipoprotein signal peptidase homolog has been discovered.

An embodiment of this invention includes the creation of a vaccine with this sequence and protein information. The proteins disclosed in this invention are extremely antigenic. Therefore, they have the potential to be extremely useful as a vaccine. The types of vaccine made available by this novel technology include a DNA vaccine, a recombinant vaccine, and a T cell epitope vaccine.

BRIEF DESCRIPTION OF THE DRAWINGS

FIG. 1 shows the three clones identified in the library screen.

DESCRIPTION OF THE PREFERRED EMBODIMENT

*E. canis* causes a devastating canine disease. Currently, there is no vaccine available to prevent this disease. This invention provides the tools necessary to develop such a vaccine. More specifically, four genes have been identified from a genomic fragment of *E. canis*, named ProA, ProB, mmpA, and a cytochrome oxidase homolog. In addition, a partial gene coding for a lipoprotein signal peptidase homolog has been found. Any of these proteins can be utilized in an embodiment of this invention to develop a vaccine.

Screening an *E. canis* Library

To identify genes in the *E. canis* genome, a genomic DNA expression library was constructed. An *E. canis* strain isolated from dogs with canine ehrlichiosis was grown in the dog cell line DH82 by a technique being known in the art, and incorporated by reference (Dawson et al., 1991; Rikihisa, 1992). The cells were harvested and the chromosomal DNA extracted as described by a technique known in the art (Chang et al., 1987; Chang et al., 1989a; Chang et al., 1989b; Chang et al., 1993a; Chang et al., 1993b). To construct the library, 200 μg of DNA was partially digested with Sau3A. DNA fragments from 3 to 8 kb were isolated and ligated to a plasmid, pHG165 (Stewart et al., 1986). The plasmids were transformed into *E. coli* TBI (Chang et al., 1987).

The library was screened with polyclonal antibodies against *E. canis*. Polyclonal antibodies were generated from dogs that had been bitten by a tick harboring *E. canis*. The polyclonal antibodies were preabsorbed with the lysate of an *E. coli* host strain. The library was plated on petri plates at a density of 1,000 colony forming units. Colonies were transferred to nitrocellulose and each filter was probed with 1 ml of the preabsorbed polyclonal antibodies. Positive colonies were identified with a second antibody consisting of an alkaline phosphatase-conjugated goat anti-rabbit IgG (Kirkegaard and Perry Laboratories, Gaithersburg, Md.), followed by color development with a substrate solution containing nitroblue tetrazolium (NBT) and 5-bromo-4-chloro-3-indolyl phosphate (BCIP). Positive clones were rescreened three times.

Three clones were isolated from this screening procedure, pCH2, 4, and 5 (FIG. 1). Within these three positive clones, an overlapping reading frame was found that codes for mmpA. The longest genomic fragment (pCH4) encodes four complete genes and one partial gene. It completely encodes the proteins ProA, ProB, mmpA, and a cytochrome oxidase homolog, as well as containing the partial sequence of a lipoprotein signal peptidase homolog. ProA and ProB are located on a single operon. Restriction endonuclease digestion mapping and DNA sequencing were done by techniques known in the art, and incorporated by reference (Chang et. al., 1987; Chang et. al., 1989a; Chang et. al., 1989b; Chang et. al., 1993a; Chang et. al., 1993b). Briefly, the DNA sequence was determined by automated DNA sequencing on the ABI PRISM Model 377 DNA system. The complete nucleotide sequences were determined on both strands by primer walking. The thermal cycling of the sequencing reactions utilized the Taq Dye Deoxy™ Terminator Cycle sequencing kit. Databases were searched for homologous proteins through the use of the BLAST network service of the National Center for Biotechnology Information (NCBI) (Althchul et al., 1990; Gish et al., 1993).

Sequence Information

The *E. canis* genes were sequenced. The cloned fragment contains 5,299 nucleotides, and codes for four proteins. There is also one partial gene at the carboxy terminus. SEQ. ID. NO. 1 is the entire nucleotide sequence. SEQ. ID. NO. 2and 3 are the translation of nucleotides 12 through 533 from SEQ. ID. NO. 1 and code for a cytochrome oxidase homolog, which was deemed ec3 and encodes a product of 174 amino acids. Cytochrome oxidase is important in virulence, and therefore is a strong candidate for use in a vaccine. SEQ. ID. NO. 4 and 5 are the translation of nucleotides 939 through 2,252 from SEQ. ID. NO. 1 and code for ProA. ProA begins 402 nucleotides downstream from the end of ec3 and encodes a product of 438 amino acids. The ProA protein shares extensive characteristics with the putrilysin family, which is a subset of metallopeptidases. The highest homology is seen in the N-terminal portion, which includes conserved putative metal binding sequence, His-X-X-Glu-His as well as conserved Glu for catalysis. ProA was also shown to share 27% of its characteristics over 284 amino acids with MPP-β. (mitochondrial processing peptidase) in *Solanum tuberosum* (Genbank accession number X80237) and 27% of its characteristics over 222 amino acids with *E. Coli* pitrilysin (Genbank accession number M17095). Many bacterial zinc proteases are also found to share homology with ProA protein, such as PqqF in *M. extrorquens* AMI where 36% of 376 amino acids are shared(Genbank accession number L43135), Y4wA in *Rhizobium* sp. where 34% of 416 amino acids are shared (Genbank accession number AE000103), 27% of 419 amino acids of the putative gene product PA0372 in *Pseudomonas aeruginosa* (Genbank accession number AE004475), and 26% of 389 amino acids of the putative gene product of HP1012 in *Helicobacter pylori*, strain 26695 are shared (Genbank accession number AE000609). SEQ. ID. NO. 6 and 7 are the translation of nucleotides 2,258 through 3,610 from SEQ. ID. NO. 1 and code for ProB. ProB begins 6 nucleotides after the end of proA and encodes a protein of 451 amino acids long. Through Blast analysis it was shown that ProB does not contain the conserved Zinc- binding domain. PrOB was shown to share homology with both subunits of the MPP subfamily and some bacterial putative zinc proteases such as PqqF, Y4wA, and the gene products of PA0372. ProB also shared homology with bacterial proteases that do not contain Zinc-ligand motif, but show similarities with the pitrilysin family, such as PqqG, Y4wB, gene product of PA0371, and the gene product of HP0657 in *M. extrorquens* AMI, *Rhizobium* sp., *P. aeruginosa*, and *H. pylori* 26695. Preliminary evidence indicates that ProA and ProB are proteases. SEQ. ID. NO. 8 and 9 are the translation of nucleotides 4,132 through 4,794 from SEQ. ID. NO. 1 and code for ORF, designated mmpA. The polypeptide that is generated consists of 221 amino acids and does not have a significant identity to any proteins found in existing databases. SEQ. ID. NO. 10 and 11 are the translation of the complementary sequence of nucleotides 4,883 through 5,299 from SEQ. ID. NO. 1 and code for the partial sequence of a lipoprotein signal peptidase homolog. Lipoprotein signal peptidases are membrane proteins, and by nature may be less desirable for vaccine development. However, this protein is still worth pursuing in the creation of a vaccine.

Structure and Expression of ProA, ProB, mmpA, Cytochrome Oxidase and the Lipoprotein Signal Structurally, MmpA is extremely hydrophobic with five transmembrane segments and three potential antigenic determinants, which are protein kinase C phosphorylation sites located in position 7 (Ser), 37 (Ser), and 213 (Ser) and one possible casein kinase II phosphorylation site in position 177 (Thr), where the above determinants were characterized by PROSITE and the PCgene programs. MmpA was localized primarily in the morula membrane. Since MmpA contains three potential phosphorylation sites, this indicates the possibility of a similar communication system as seen by phosphorylation of one of the chlamydial inclusion membrane proteins, *IncA. E. canis* grown in vitro (DH82 cells) expressed MmpA, furthermore, sera obtained from dogs that were naturally infected and experimentally infected with *E. canis* recognized MmpA, which confirms that in vivo and in vitro expression of MmpA as well as the antigenicity of MmpA. The above two results indicate that MmpA is capable of stimulating an immune response, which is necessary for a vaccine to be effective. However, *E. canis* is an intracellular organism, cell mediated immunity is more important in protecting the dog against this type of infection then humoral immunity and it may be possible to direct these antigens toward a predominant Th1 response using an appropriate adjuvant. The mmpA gene was found in *E. canis* and *E. chaffeenis* but was not present in the HGE agent. However, the MmpA protein was not expressed by *E. chaffeenis* on a western blot. *E. canis* with MmpA caused cells to lyse, indicating the presence of MmpA protein, where *E. chaffeenis* with MmpA did not lyse. This result lends to the conclusion that the MmpA protein may be useful for serodiagnosis in differentiating *E. canis* and *E. chaffeenis*. Furthermore, MmpA, ProA, and ProB proteins can be used as antigens in ELISA or Western blot analysis to perform a diagnosis of an *E. canis* infection in animals.

Structurally, ProA and ProB are very similar except for the fact that ProA contains a catalytic zinc-binding motif and ProB does not contain any catalytic residues. ProA and ProB were localized to the soluble cytoplasmic and periplasmic protein portion, where a tiny amount of ProA was detectable in the inner membrane fraction of the bacterial fractions that were collected to do subcellular fractionation to determine a subcellular location. *E. canis* and *E. chaffeenis* infected DH82 cells both lysed that contained anti-rProA antibodies, showing that both *E. canis* and *E. chaffeenis* express ProA in culture. Furthermore, both naturally and experimentally infected dogs with *E. canis* infected DH82-cells recognize rProA and rProB lending to the conclusion that ProA and ProB are expressed in vivo and in vitro. However, ProB was not delectable in a western blot using anti-rProB antibodies with *E. chaffeenis*. *E. canis* did detect anti-rProB antibodies. This result shows that ProB may serve as a tool for serological differentiation of *E. canis* and *E. chaffeenis*. Antisera from naturally and experimentally infected dogs with *E. canis* contained antibodies recognizing rProA and rProB. Serum from an uninfected dog did not recognize either of the two proteins. Immunofluorescence staining of *E. canis* in DH82 cells with rabbit anti-rProA arid anti-rProB sera was performed, both ProB and ProA antiserum strongly label the intracellular ehrlichial organisms, showing that ProA and ProB can serve as target antigens and that anti-rProA and anti-rProB sera can be used for indirect immunofluorcscent assays (IFA) diagnosis. Recombinant ProB can be used as an antigen in ELISA or Western blot analysis to perform a diagnosis of an *E. canis* infection in animals.

Overexpression of ProA, ProB, ORF, Cytochrome Oxidase and the Lipoprotein Signal Peptidase Homolog The *E. canis* antigens are overexpressed in a T7 promoter plasmid. The pRSET vector allows high level expression in *E. coli* in the presence of T7 RNA polymerase, which has a strong affinity for the T7 promoter. After subcloning the antigen genes into the pRSET vector, the subclones are transformed into an F' *E. coli* JM109 strain. For maximum protein expression, the transformants are cultured to O.D. 600=0.3, exposed to IPTG (1 mM) for one hour and then transfected with M13/T7 bacteriophages at a multiplicity of infection (MOI) of 5-10 plaque forming units (pfu) per cell. Time course studies indicate that maximum induction is reached two hours after induction.

The pellet is harvested by centrifugation and the cells are resuspended in 6M Guanidinium (pH 7.8). Cells are ruptured by French press and the total lysate is spun at 6000 rpm to separate cell debris by a technique known in the art, and hereby incorporated by reference (Chang et al., 1993c). Immobilized metal ion affinity chromatography (IMIAC) is used to purify each of the proteins under denaturing conditions as described by the manufacturer (Invitrogen, San Diego, Calif.). The protein samples are separated by SDS-polyacrylamide gel electrophoresis (SDS-PAGE) and visualized after staining with coomassie blue.

Diagnosis Techniques: KELA ELISA. Western Blotting (Immunoblots), and PCR

The recombinant ProA, ProB, and MmpA proteins are useful diagnostic agents. One diagnostic technique where the ProA, ProB, and MmpA proteins are used is kinetic enzyme linked immunosorbent assay (KELA ELISA), as described by a technique known in the an (Appel et al., 1993; Chang et al., 1995). KELA measures the levels of serum antibodies to *E. canis* that is present. In this diagnostic technique, diluted serum (1:100 dilution) is added to duplicate wells in microliter plates that contain antigens of MmpA, ProA, and ProB. The antigens are prepared by French-pressing them. The bound antibodies are then detected by using second antibodies of a goat anti-canine antibody of heavy and light chain specificity conjugated to horseradish peroxidase (HRP). Color development is seen and measured using the chromogen tetramethylbenzidine with $H_2O_2$ as a substrate, which is measured kinetically and expressed as the slope of the reaction rate between the enzyme and substrate solution. Each unit of slope is designated as a KELA unit. The cutoff point between positive and negative samples is then confirmed by Western blotting against French-pressed *E. canis*.

The procedure for Western blot analysis, as described by a technique known in the art (Appel et al., 1993; Chang et al., 1995), is performed. Recombinant ProA, ProB, and MmpA are used as antigens and are subjected to sodium dodecyl sulfate-polyacrylamide gel electrophoresis (SDS-PAGE). Western blot analysis is performed in a miniblotter. Test sera from experimental animals are used as a first antibody, followed by goat anti-dog IgG conjugated to HRP as a second antibody. Bands are developed by using substrates, such as 24 μg of 4-chloro-1-naphthol in 8 ml of methyl alcohol, 40 ml of Tris-buffer solution, and 24 μl of 30% $H_2O_2$.

Another diagnostic technique recombinant ProA, ProB, and MmpA proteins can be used for is PCR diagnosis. The DNA from biopsy samples of skin or from post mortem tissues or blood are extracted as described by a technique known in the art (Chang et al., 1998a; Chang et al., 1998b). To prevent contamination of the mixtures and samples, DNA extraction, amplification, and detection of PCR products are all performed in different rooms. Amplification of *E. canis* MmpA, ProA, or ProB-specific target sequences is carried out in a 50-μl reaction mixture. As a positive control, *E. canis* genomic DNA is used. As a negative control distilled water is used. The reaction mixture is then put through 40 cycles of amplification using an automated DNA thermal cycler. Each cycle involves healing the reaction mixture to 94° C. from 1 minute, to cause the DNA to denature; cooling of the reaction mixture to 69° C. for 1 minute, to allow the primers to anneal; and then heating the reaction mixture to 72° C. for 2minutes, to allow primer extension to occur. Gel electrophoresis on a 1.5% agarose gel is done in order to get visualization of the PCR amplification products.

Vaccine Development

Prior to the present invention, no vaccine against *E. canis* had been developed. *E. canis* is endemic in dogs and closely related canidae in many parts of the world. Dogs in North America are also increasingly at risk and the application of the present invention can potentially save the lives of thousands of dogs each year. An *E. canis* vaccine that can elicit cell-mediated immunity against this tick-borne disease of dogs is desperately needed.

DNA Vaccine

A DNA vaccine is constructed by subcloning the gene of interest into a eukaryotic plasmid vector. Candidate vectors include, but are not limited to, pcDNA3, pCI, VR1012, and VR1020. This construct is used as a vaccine.

Each of the newly identified genes, ProA, ProB, mmpA, the cytochrome oxidase homolog, or the partial lipoprotein signal peptidase homolog can be used to create a DNA vaccine (reviewed in Robinson, 1997). In addition, any immunologically active portion of these proteins is a potential candidate for the vaccine. A plasmid containing one of these genes in an expression vector is constructed. The gene must be inserted in the correct orientation in order for the genes to be expressed under the control of eukaryotic promoters. Possible promoters include, but are not limited to, the cytomegalovirus (CMV) immediate early promoter, the human tissue plasminogen activator (t-PA) gene (characterized in Degen et al., 1986), and the promoter/enhancer region of the human elongation factor alpha (EF-1 α) (characterized in Uetsuki et al., 1989). Orientation is identified by restriction endonuclease digestion and DNA sequencing.

Expression of these gene products is confirmed by indirect immunofluorcscent staining of transiently transfected COS cells, CHO cells, or other suitable cells. The same plasmid without these genes is used as a control. Plasmid DNA is transformed into *Escherichia coli* DH5α. DNA is purified by cesium chloride gradients and the concentration is determined by a standard protocol being known in the art, and incorporated by reference (Nyika et al., 1998).

Once the DNA is purified, the vector containing the insert DNA can be suspended in phosphate buffer saline solution and directly injected into dogs. Inoculation can be done via the muscle with a needle or intraveneously. Alternatively, a gene gun can be used to transport DNA-coated gold beads into cells by a technique known in the art, and hereby incorporated by reference (Fynan et al., 1993). The rationale behind this type of vaccine is that the inoculated host expresses the plasmid DNA in its cells, and produces a protein that raises an immune response. Each of the newly identified genes can be used to create a vaccine by this technique.

CpG molecules can be used as an adjuvant in the vaccine. This technique is known in the art, and is hereby incorporated by reference (Klinman et al., 1997). Adjuvants are materials that help antigens or increase the immune response to an antigen. The motifs consist of an unmethylated CpG dinucleotide flanked by two 5' purines and two 3' pyrimidines. Oligonucleotides containing CpG motifs have been shown to activate the immune system, thereby boosting an antigen-specific immune response. This effect can be utilized in this invention by mixing the CpG oligonucleotides with the DNA vaccine, or physically linking the CpG motifs to the plasmid DNA.

Immunofluorescence staining of *E. canis* in DH82 cells with rabbit anti-rProA and anti-rProB sera was performed, both ProB and ProA antiserum strongly label the intracellular ehrlichial organisms, showing that ProA and ProB can serve as target antigens and that anti-rProA and anti-rProB sera can be used for indirect immunofluorescent assays (IFA) diagnosis, making the DNA vaccine a viable option to combat this disease.

Recombinant Vaccine

In order to develop a recombinant vaccine, each of the genes is individually subcloned into overexpression vectors, and then purified for vaccine development. ProA, ProB, mmpA, the cytochrome oxidase homolog, or the partial lipoprotein signal peptidase homolog is expressed in a plasmid with a strong promoter such as the tac, T5, or T7 promoter. Alternatively, immunologically active fragments of these proteins are used in the development of a vaccine. Each of these genes is subcloned into a plasmid and transformed into an *E. coli* strain as described above.

The recombinant protein is overexpressed using a vector with a strong promoter. Vectors for use in this technique include pREST (Invitrogen Inc., Calif.), pKK233-3 (Pharmacia, Calif.), and the pET system (Promega, Wis.), although any vector with a strong promoter can be used. After overexpression, the proteins are purified and mixed with adjuvant. Potential adjuvants include, but are not limited to, aluminum hydroxide, QuilA, or Montamide. The purified protein is used as immunogen to vaccinate dogs by a technique being known in the art, and incorporated by reference (Chang et al., 1993c; Chang et al., 1995). Briefly, the individual protein is expressed and purified from *E. coli*. Then, the dogs are injected intramuscularly or subcutaneously with the purified recombinant vaccine and adjuvant. This injection elicits an immune response.

T Cell Epitope Vaccine

Direct cell cytotoxicity mediated by $CD8^+$ T lymphocytes (CTL) is the major mechanism of defense against intracellular pathogens. These effector lymphocytes eliminate infected cells by recognizing short peptides associated with MHC class I molecules on the cell surface. Exogenous antigens enter the endosomal pathway and are presented to $CD4^+$ T cells in association with class II molecules whereas endogenously synthesized antigens are presented to $CD8^+$ T cells in association with MHC class I molecules. *E. canis* is an intracellular pathogen that resides in monocytes and macrophages. The present invention develops novel ways of generating an *E. canis*-specific CTL response that would eliminate the organism from monocytes or macrophages of infected animals.

A strategy for increasing the protective response of a protein vaccine is to immunize with selective epitopes of the protein. The rationale behind this is that an epitope vaccine contains the most relevant immunogenic peptide components without the irrelevant portions. Therefore, a search is performed for the most highly antigenic portions of the newly identified proteins.

To identify T-cell epitopes from the newly discovered proteins, an initial electronic search for homologous sequences to known T-cell epitopes is performed. In addition, extensive T-cell epitope mapping is carried out. Each of the proteins, ProA, ProB, mmpA, the cytochrome oxidase homolog, and the partial lipoprotein signal peptidase homolog, is tested for immunogenic peptide fragments. Mapping of T cell epitopes by a technique known in the art is hereby incorporated by reference (Launois et al., 1994; Lee and Horwitz, 1999). Briefly, short, overlapping peptide sequences (9-20 amino acids) are synthesized over the entire length of the protein in question. These short peptide fragments are tested using healthy dogs, which have been immunized with the protein of interest. Peripheral blood mononuclear cells from the dogs are tested for T cell stimulatory and IFN-γ inducing properties. Those fragments which elicit the strongest response are the best candidates for a T-cell epitope vaccine.

Once fragments are identified which will make the best epitopes, a recombinant adenylate cyclase of *Bordetella bronchiseptica* is constructed carrying an *E. canis* CD8+ T cell epitope. The adenylate cyclase toxin (CyaA) of *Bordetella bronchiseptica* causes disease in dogs and elicits an immune response. In addition, CyaA is well suited for intracytoplasmic targeting. Its catalytic domain (AC), corresponding to the N-terminal 400 amino acid residues of the 1,706-residue-long protein, can be delivered to many eukaryotic cells, including cells of the immune system. Also, toxin internalization is independent of receptor-mediated endocytosis, suggesting that the catalytic domain can be delivered directly to the cytosol of target cells through the cytoplasmic membrane. The *Pseudomonas aeruginosa* exotoxin A (PE) is another toxin which could be used in this procedure to deliver peptides or proteins into cells, by a technique known in the art, and hereby incorporated by reference (Donnelly et al., 1993).

Foreign peptides (16 residues) have been inserted into various sites of the AC domain of CyaA without altering its stability or catalytic and calmodulin-binding properties. Thus, protein engineering allows the design and delivery of antigens that specifically stimulate CTLs. The induction of specific CD8+ T cells can play an important role in canine ehrlichiosis control due to the intracellular persistence of *E. canis* in monocytes.

The adenylate cyclase (AC) toxin (cya) gene of *B. bronchiseptica* has been cloned. A synthetic double-stranded oligonucleotide encoding a 9 to 20 amino acid class IT cell epitope of either ProA, ProB, mmpA, the cytochrome oxidase homolog, or the partial lipoprotein signal peptidase homolog, is designed according to *B. bronchiseptica* codon usage. The complementary oligonucleotides are inserted in the hypervariable region of the cloned AC-coding sequence of the cya. This technique is known in the art in other systems, and is incorporated by reference (Sebo et al., 1995; Guermonprez et al., 1999).

Recombinant plasmids carrying the chimeric cya gene are sequenced to determine the copy number and orientation of the inserted epitope. A plasmid with a complete copy of the insert that specifies the T-cell epitope (CD8+) in the correct orientation is chosen from the sequenced plasmids. The ability of the new chimeric protein to enter eukaryotic cells is necessary to ensure intracellular targeting of the epitopes (Fayolle et al., 1996).

A vaccine can be created in one of two ways. Recombinant chimeric protein can be purified and used to inoculate dogs. Alternatively, an attenuated *B. bronchiseptica* strain that carries a T-cell epitope or *E. canis* gene by in-frame insertion into adenylate cyclase is created by allelic-exchange. Allelic-exchange is a technique known in the art, and is hereby incorporated by reference (Cotter and Miller, 1994).

Finally, protection against *E. canis* infection in dogs vaccinated with the adenylase cyclase- ProA, ProB, mmpA, cytochrome oxidase homolog, or lipoprotein signal peptidase homolog chimeric protein is determined. Wild type and recombinant ACs and CyAs are diluted to working concentrations in PBS and the chimeric protein is injected into dogs either intramuscularly or subcutaneously. Alternatively, the T-cell epitope is inserted into the adenylate cyclase gene of an attenuated *B. bronchiseptica* strain in frame; and the dogs are given the live bacteria.

Recombinant antigens are promising candidates for human and animal vaccination against various pathogens. However, a serious drawback is the poor immunogenicity of recombinant antigens as compared to native antigens. A major challenge in the development of a new recombinant vaccine is, therefore, to have a new adjuvant system that increases the immunogenicity of antigens. Cytokines are powerful immunoregulatory molecules. Cytokines which could be used as adjuvants in this invention include, but are not limited to, IL-12 (interleukin-12), GM-CSF (granulocyte-macrophage colony stimulating factor), IL-1β (interleukin-1β) and γ-IFN (gamma interferon).

These cytokines can have negative side effects including pyrogenic and/or proinflammatory symptoms in the vaccinated host. Therefore, to avoid the side effects of a whole cytokine protein, an alternate approach is to use synthetic peptide fragments with the desired immunostimulatory properties. The nonapeptide sequence VQGEESNDK of IL-1β protein is endowed with powerful immuno-enhancing properties, and is discussed here to illustrate the use of a cytokine to increase immunogenicity.

This nonapeptide is inserted into the ProA, ProB, mmpA, the cytochrome oxidase homolog, or the partial lipoprotein signal peptidase homolog protein and its immunogenicity is compared to that of the native protein. Reportedly, the insertion of this sequence into a poorly immunogenic recombinant antigen increases the chance of a strong protective immune response after vaccination. This peptide could enhance the in vivo immune response against both T-dependent and T-independent antigens. The canine IL-1β sequence may mimic many immunomodulatory activities of the entire molecule of IL-1β while apparently lacking many of its undesirable proinflammatory properties. This strategy is employed to increase the immunogenicity of ProA, ProB, mmpA, cytochrome oxidase, the partial lipoprotein signal peptidase homolog and other *E. canis* antigens.

Plasmid pYFC199 is derived from a pBR322 plasmid by the insertion of a fragment that includes the ProA, ProB, mmpA, the cytochrome oxidase homolog, or the partial lipoprotein signal peptidase protein from *E. canis*. This plasmid contains a unique HindIII site where in-Frame insertions encoding exogenous sequences can be inserted. Two complementary oligonucleotides, SEQ. ID. NO. 12 and SEQ. ID. NO. 13, that encode the canine IL-1β 163-171 peptide are annealed, cut with HindIII, and inserted into the pYFC199 Hind III site. The recombinant plasmid carrying the chimeric IL-1β gene is sequenced to determine the orientation of the inserted epitope.

The efficacy of the recombinant proteins as vaccines is tested in dogs. The purified protein is injected intraperitoneally into dogs. Specific pathogen free (SPF) dogs are divided into five groups: one group is given recombinant adenylate cyclase of *Bordetella bronchiseptica* carrying *E. canis* CD8+ T cell epitopes derived from ProA, ProB, mmpA, cytochrome oxidase homolog, or the partial lipoprotein signal peptidase homolog, one group is given recombinant adenylate cyclase of *Bordetella bronchiseptica* as a control, one group is given the ProA, ProB, mmpA, cytochrome oxidase homolog, or the partial lipoprotein signal peptidase homolog protein plus a canine IL-1β 163-171 insert, one group is given a T cell epitope derived from ProA, ProB, mmpA, cytochrome oxidase homolog, or the partial lipoprotein signal peptidase homolog alone, and the last group is given PBS as a negative control.

All animals are vaccinated (30-40 μg each) two times. The dogs are challenged ten days after the last vaccination with $10^7$ *E. canis*. At day five postchallenge, approximately 1 ml blood from each dog is collected in an EDTA lube. Whether the vaccinated groups eliminate the organisms as compared to that of the control group is tested by culture and PCR. Two primers derived from the genes cloned can be used to amplify the gene product from the tissues or blood samples from these dogs. The internal primer can also be designed for use as an oligonucleotide probe to hybridize the PCR gene product.

This invention provides a badly needed vaccine against the *E. canis* bacterium. The vaccine can be used to protect dogs throughout the world from canine monocytic ehrlichiosis.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A recombinant protein comprising a protein selected from the group consisting of:
   a) a protein having the amino acid sequence as shown in SEQ. ID. NO. 3 wherein the protein elicits an immune response against *E. canis;*
   b) a protein having the amino acid sequence as shown in SEQ. ID. NO. 5 wherein the protein elicits an immune response against *E. canis;*
   c) a protein having the amino acid sequence as shown in SEQ. ID. NO. 7 wherein the protein elicits an immune response against *E. canis;*
   d) a protein having the amino acid sequence as shown in SEQ. ID. NO. 9 wherein the protein elicits an immune response against *E. canis;* and
   e) a protein having the amino acid sequence as shown in SEQ. ID. NO. 11 wherein the protein elicits an immune response against *E. canis.*

2. An immunogenic composition comprising a recombinant protein of claim 1.

3. The immunogenic composition of claim 2 comprising an adjuvant.

4. The immunogenic composition of claim 2 wherein the immunogenic composition is administered into a host by a method selected from the group consisting of:
   a) intramuscular injection; and
   b) subcutaneous injection.

5. A method for making an immunogenic composition against *E. canis* comprising:
   a) selecting a vector capable of expressing a recombinant protein inserted into the vector;
   b) inserting a recombinant DNA into the vector such that the recombinant protein is expressed when the vector is transformed into a bacterial strain wherein the DNA is selected from the group consisting of:
      i) a recombinant DNA that encodes a protein having the amino acid sequence as shown in SEQ. ID. NO.3;
      ii) a recombinant DNA that encodes a protein having the amino acid sequence as shown in SEQ. ID. NO.5;
      iii) a recombinant DNA that encodes a protein having the amino acid sequence as shown in SEQ. ID. NO.7;
      iv) a recombinant DNA that encodes a protein having the amino acid sequence as shown in SEQ. ID. NO.9; and
      v) a recombinant DNA that encodes a protein having the amino acid sequence as shown in SEQ. ID. NO. 11; and
   c) harvesting the recombinant protein from the bacterial strain.

6. The method of claim 5, comprising the step of mixing the recombinant protein with an adjuvant.

7. The method of claim 5, wherein the immunogenic composition further comprises a promoter selected from the group consisting of:
   a) tac;
   b) T5; and
   c) T7.

8. The method of claim 5, wherein the bacterial strain is *E. coli.*

9. The method of claim 5, wherein the vector is selected from the group consisting of:
   a) pREST;
   b) pET; and
   c) pKK233-3.

10. An immunogenic composition selected from the group consisting of
    a) a recombinant DNA that encodes a protein having the amino acid sequence as shown in SEQ. ID. NO. 3 wherein the protein elicits an immune response against *E. canis;*
    b) a recombinant DNA that encodes a protein having the amino acid sequence as shown in SEQ. ID. NO. 5 wherein the protein elicits an immune response against *E. canis;*
    c) a recombinant DNA that encodes a protein having the amino acid sequence as shown in SEQ. ID. NO. 7 wherein the protein elicits an immune response against *E. canis;*
    d) a recombinant DNA that encodes a protein having the amino acid sequence as shown in SEQ. ID. NO. 9 wherein the protein elicits an immune response against *E. canis;* and
    e) a recombinant DNA that encodes a protein having the amino acid sequence as shown in SEQ. ID. NO. 11 wherein the protein elicits an immune response against *E. canis.*

11. An immunogenic composition comprising a vector, wherein:
   the vector is capable of expressing an isolated recombinant DNA comprising the isolated recombinant DNA inserted into the vector such that a recombinant protein is expressed when the vector is provided in an appropriate host wherein the isolated recombinant DNA is selected from the group consisting of:
   a) SEQ. ID. NO. 2, wherein SEQ. ID. NO. 2 encodes a protein having the amino acid sequence as shown in SEQ. ID. NO. 3 and wherein the protein elicits an immune response against *E. canis*;
   b) SEQ. ID. NO. 4, wherein SEQ. ID. NO. 4 encodes a protein having the amino acid sequence as shown in SEQ. ID. NO. 5 and wherein the protein elicits an immune response against *E. canis*;
   c) SEQ. ID. NO. 6, wherein SEQ. ID. NO. 6 encodes a protein having the amino acid sequence as shown in SEQ. ID. NO. 7 and wherein the protein elicits an immune response against *E. canis*;
   d) SEQ. ID. NO. 8, wherein SEQ. ID. NO. 8 encodes a protein having the amino acid sequence as shown in SEQ. ID. NO. 9 and wherein the protein elicits an immune response against *E. canis*; and
   e) SEQ. ID. NO. 10, wherein SEQ. ID. NO. 10 encodes a protein having the amino acid sequence as shown in SEQ. ID. NO. 11 and wherein the protein elicits an immune response against *E. canis*.

12. A method for generating an immune response in a canine host comprising the step of injecting the immunogenic composition of claim 2 into the canine host.

13. The method of claim 12 wherein the step of injecting is selected from the group consisting of:
   a) injecting intramuscularly; and
   b) injecting subcutaneously.

14. A method for generating an immune response in a canine host comprising the step of injecting the immunogenic composition of claim 11 into the canine host.

15. The method of claim 14 wherein the step of injecting is selected from the group consisting of:
   a) injecting intramuscularly;
   b) injecting intravenously; and
   c) injecting via gene gun.

\* \* \* \* \*

SEQUENCE LISTING

```
<160> NUMBER OF SEQ ID NOS: 14

<210> SEQ ID NO 1
<211> LENGTH: 5299
<212> TYPE: DNA
<213> ORGANISM: Ehrlichia canis
<220> FEATURE:
<221> NAME/KEY: gene
<222> LOCATION: (1)..(5299)

<400> SEQUENCE: 1
gatcaaataa aatgaaacca agaataagaa acactattta tggattaata gcaataatac     60
tatctatgat atgtttagtg tacgcttctg taccactata tagtatattt tgtaaagtaa    120
caggttatgg aggtacagta agaacaagta atatatcaaa ttctaaaata ggtaacacta    180
ttattaaagt cagatttaat gcagatatac acaaacaact gccatggaaa ttctatccag    240
aagtatctca tgtatttgta aaaccaggag aacaaaaatt gattttctac cgcgcagaaa    300
atctacttga tgaggacact tcaggaatgg ctgtatataa tgttacacca cataaagtag    360
gaaaatattt taataaggta gcttgttttt gtttcaccaa acaaacatta taccctcatc    420
aaaaaactat aatgccagta tcatttttta tagatccagc catagaaaca gatcctgaaa    480
ctgctgacgt aaaactcatc actctttcat atgtattctt taagtacaaa gaataaactt    540
catataccgt acattataaa ctgattaaaa aaaataacta ttaatattga gcaaaataat    600
ttatctattc aacagattct tttcaattag agagtattca aaaacactac aactactgct    660
tgcaactttc tatcactgat atataaaagt gaaataaatt taaaaaactt tagttttaat    720
agaagaattt tattaaaagc tttgaatcaa atttaattac tgatataaaa atactattaa    780
acattaacaa tgcttaatta aagtattatt atttacctta atttcataac ctttattaac    840
aatttcataa taaaaatact ttactcttat ttttttatca cttgatatta ttaaataatc    900
atataaactc ccaaataaac tattgcaagg ttatggtaat gatgaaattt tttacttgtt    960
ttttcatagt tttcttaaca atagccaatc atgctttatc ctttaacatt aaagttacac   1020
atgaaaaatt agataatgga atggaagtat acgtgattcc aaatcatcgc gcaccagcag   1080
tcatgcacat ggtattatac aaagtcggtg gaactgatga tccagtagga tactctggat   1140
tagcacattt ttttgaacac ttaatgttta gtggaacaga aaaatttcct aatctcatca   1200
gcacacttag taatataggc ggaaatttca atgcaagcac atctcaattt tgtactatat   1260
actacgaatt aataccaaaa caatatttat ctcttgcaat ggatattgaa tcagacagaa   1320
tgcagaattt taaggttacc gacaaagcat taataagaga acaaaaggta gtcttagaag   1380
aaagaaaaat gagagttgaa agccaagcaa aaaacatact agaagaagaa atggaaaatg   1440
cattttatta caatggatat ggcagaccag tagtaggatg ggaacatgaa attagcaact   1500
acaacaaaga agttgctgaa gcctttcata agctacatta tagtcctaat aatgctatat   1560
taattgtaac tggagatgca gatccacaag aagtaatcac acttgcaaaa caatactatg   1620
ggaaaatacc atctaataat aagaaacctt caagtcaagt tagggtagaa ccaccgcata   1680
```

```
aaacaaatat gactttaaca ttaaaagaca gttcagtaga aatcccagaa ctgtttttaa    1740
tgtatcaaat accaaatggt attaccaata aaaactacat acttaacatg atgttagcag    1800
aaatactcgg tagtggtaaa ttcagcctgc tttacaatga tttggtaatt aacaatccaa    1860
tagttacatc gataaaaaca gattataatt acttaactga cagcgataat tacctttcca    1920
ttgaagctat acctaaaaac gggatctcta cagaagctgt agaacaagaa attcataaat    1980
gtataaataa ttatttagaa aatggaattt cagcagaata tttagaaagt gcaaagtata    2040
aagtaaaagc acatttaact tatgcatttg acggactaac tttcatatca tattttatg     2100 gcatgcatct aatactagga gtaccgctat cagaaatcag taatatttac gataccatag    2160
acaaagtaag tatccaagat gttaactccg ctatggaaaa tatctttcaa aacaatataa    2220
gattaaccgg gcatttatta cctaatggag aatagttatg agaaacatat tgtgttacac    2280
attaatattg attttctttt cattcaatac atatgcaaat gatctcaata ttaacataaa    2340
agaagctaca actaaaaata aaatacacta tctatatgtt gaacatcata acctaccaac    2400
aatttcctta aaatttgcat tcaagaaagc aggatacgct tatgatgcct ttgataagca    2460
aggacttgca tactttacat caaaaatatt aaacgaagga tcaaaaaaca actatgctct    2520
cagttttgca caacaattag aaggcaaagg tatagactta aaatttgata tagacctaga    2580
caatttttat atatcattaa aaaccttatc agaaaacttt gaagaagccc tagtttttact  2640 cagtgattgc atattcaaca ccgtcacaga tcaagaaata ttcaatagaa aatagcaga    2700 acagattgca catgttaaat cattatattc tgctcctgaa tttatagcta caacagaaat    2760
gaatcacgct atattcaaag ggcacccata ttctaacaaa gtttacggga cattaaatac    2820
aatcaataat atcaaccagg aagacgttgc attatatata aaaaatagtt ttgacaagga    2880
acaaatcgtt atcagcgcag caggagatgt agatccaaca cagctatcaa atttactaga    2940
taaatatatt ctttccaaat tgccatctgg taataacaaa aataccatac cagatacgac    3000
tgttaataga gaagacacat tattatatgt acagagagat gtaccacaaa gtgtcataat    3060
gtttgctaca gacacagtac catatcacag caaagactat catgcatcaa acttgttcaa    3120
tactatgcta ggcggattaa gtctcaattc aatattaatg atagaattaa gagacaagtt    3180
aggattaaca taccatagta gcagttcact atctaacatg aatcatagta atgtgctatt    3240
tggtacaata ttcactgata ataccacagt aacaaaatgt atatccgtct taacagatat    3300
tatagagcac attaaaaagt atggagttga tgaagacact tttgcaattg caaaatctag    3360
tattaccaac tcttttattt tatctatgtt aaataacaat aatgttagtg agatattgtt    3420
aagcttacaa ttacacgatc tagatccgag ttatattaat aaatacaatt cttactacaa    3480
agcaataaca atagaagaag taaataaaat tgccaagaaa attttatcta atgaattagt    3540
aataattgaa gtaggaaaaa acaataacat aaatggcaaa caaatagatg ctaaaaaaca    3600
catacttggt taagtataca ggttattgta tttactacaa gtattctatt aggttgtatt    3660
aagtaagtat aagtagcttc aatcaaataa aaaaacatta accaaagtgt tagctctacc    3720
ggagaagctt attataagct tttaacctgg gataaatatga agttttgcta atgttaagca   3780
aaaaattagt aatcacaata tcaaattttc tttacaggat tatattgtga cctaccataa    3840
caacttatat ttagaaaatg acaacagata cacacatcaa taaattatca ctacaattca    3900
attaataaaa caatgagtat ttttacttaa ttatttaatt ttatttttta aaataaaatt    3960 acaatttttac ttactcaata aaagcagtta tactaccaag tattggatgg tattaatcgg   4020
agcaattact acttaatagt atagctgttg acaagccgca atctgcggtt cttgacaaaa    4080
```

-continued

```
taatactaat cagttaaaat tttgaagtgt tcaccataa tggtattatt tatgaaagct    4140
catagcacaa gtatacggaa cttttcagcct ttagaaagag ctgctataat cattgcagtg   4200
ttaggtttag ctgcattctt gtttgctgct gctgcctgca gtgatcgttt ccaaagattg    4260
caattaacaa atccatttgt aatagcagga atggttggcc ttgcagttct tttagttgct    4320
tccttaacag cagcattaag tatatgctta actaaaagta agcaagtcac acaacatgct    4380
attagacatc gctttggata cgagtcaagc acttcttctt ctgtactgct tgcaatatca    4440
ataatttctt tattacttgc tgcagcattt tgtggaaaga aatgggtaa tgacaaccca    4500 gatctattct ttagcaagat gcaagaactc tccaatccac ttgttgttgc agctattgta    4560 gccgttctg ttttcctact ctcattcgta atgtatgctg caaagaacat tataagtcca    4620
gataaacaaa ctcacgttat tatattatct aatcaacaaa ctatagaaga agcaaaagta    4680
gatcaaggaa tgaatatttt gtcagcagta ctcccagcag ctggcattga catcatgact    4740
atagcttctt gtgacatttt agcagtgagc agccggggat cctctcagca tcaatagatt    4800
tatgttttag cctgtattca cctttttatt aggtgttgta tcgtttcttt atataagtgt    4860
gttatattat ataaaacatc taggagttac agttaatttg tttcatgtgg ttattactct    4920
ttgccattat tattactata cctaaaaata taaaagaatc cgccaggttg aatacaggcc    4980
aatgtaagtt attgatataa aaatctataa aatcatagac agcaccatat cttattctat    5040
ctatgatatt tcctattgac cccccaataa tgattacaag aggtaatcta taatgtggct    5100
gtactataaa taagtagcat aaaacacaag taatcaaaat cgagatacta caaaaaacaa    5160
cattactata ttcaaagtta tttaatatac caaaactaat tccagcattc cacactgtag    5220
taaagcgcaa gaagcttaat atctctatta cacctttatc tcctatcaaa tttactacat    5280
accatttact tacctgatc                                                  5299
```

<210> SEQ ID NO 2
<211> LENGTH: 522
<212> TYPE: DNA
<213> ORGANISM: Ehrlichia canis
<220> FEATURE:
<221> NAME/KEY: CDS
<222> LOCATION: (1)..(522)
<223> OTHER INFORMATION: Protein translated from nucleotides 12 through
      533 (cytochrome oxidase homolog).

<400> SEQUENCE: 2

```
atg aaa cca aga ata aga aac act att tat gga tta ata gca ata ata    48
Met Lys Pro Arg Ile Arg Asn Thr Ile Tyr Gly Leu Ile Ala Ile Ile
1               5                   10                  15 cta tct atg ata tgt tta gtg tac gct tct gta cca cta tat agt ata    96
Leu Ser Met Ile Cys Leu Val Tyr Ala Ser Val Pro Leu Tyr Ser Ile
            20                  25                  30 ttt tgt aaa gta aca ggt tat gga ggt aca gta aga aca agt aat ata   144
Phe Cys Lys Val Thr Gly Tyr Gly Gly Thr Val Arg Thr Ser Asn Ile
        35                  40                  45 tca aat tct aaa ata ggt aac act att att aaa gtc aga ttt aat gca   192
Ser Asn Ser Lys Ile Gly Asn Thr Ile Ile Lys Val Arg Phe Asn Ala
    50                  55                  60 gat ata cac aaa caa ctg cca tgg aaa ttc tat cca gaa gta tct cat   240
Asp Ile His Lys Gln Leu Pro Trp Lys Phe Tyr Pro Glu Val Ser His
65                  70                  75                  80 gta ttt gta aaa cca gga gaa caa aaa ttg att ttc tac cgc gca gaa   288
Val Phe Val Lys Pro Gly Glu Gln Lys Leu Ile Phe Tyr Arg Ala Glu
                85                  90                  95 aat cta ctt gat gag gac act tca gga atg gct gta tat aat gtt aca   336
```

```
                Asn Leu Leu Asp Glu Asp Thr Ser Gly Met Ala Val Tyr Asn Val Thr
                                100                 105                 110 cca cat aaa gta gga aaa tat ttt aat aag gta gct tgt ttt tgt ttc      384
Pro His Lys Val Gly Lys Tyr Phe Asn Lys Val Ala Cys Phe Cys Phe
            115                 120                 125 acc aaa caa aca tta tac cct cat caa aaa act ata atg cca gta tca      432
Thr Lys Gln Thr Leu Tyr Pro His Gln Lys Thr Ile Met Pro Val Ser
        130                 135                 140 ttt ttt ata gat cca gcc ata gaa aca gat cct gaa act gct gac gta      480
Phe Phe Ile Asp Pro Ala Ile Glu Thr Asp Pro Glu Thr Ala Asp Val
145                 150                 155                 160 aaa ctc atc act ctt tca tat gta ttc ttt aag tac aaa gaa              522
Lys Leu Ile Thr Leu Ser Tyr Val Phe Phe Lys Tyr Lys Glu
                165                 170

<210> SEQ ID NO 3
<211> LENGTH: 174
<212> TYPE: PRT
<213> ORGANISM: Ehrlichia canis

<400> SEQUENCE: 3

Met Lys Pro Arg Ile Arg Asn Thr Ile Tyr Gly Leu Ile Ala Ile Ile
1               5                   10                  15

Leu Ser Met Ile Cys Leu Val Tyr Ala Ser Val Pro Leu Tyr Ser Ile
            20                  25                  30

Phe Cys Lys Val Thr Gly Tyr Gly Gly Thr Val Arg Thr Ser Asn Ile
        35                  40                  45

Ser Asn Ser Lys Ile Gly Asn Thr Ile Ile Lys Val Arg Phe Asn Ala
    50                  55                  60

Asp Ile His Lys Gln Leu Pro Trp Lys Phe Tyr Pro Glu Val Ser His
65                  70                  75                  80

Val Phe Val Lys Pro Gly Glu Gln Lys Leu Ile Phe Tyr Arg Ala Glu
                85                  90                  95

Asn Leu Leu Asp Glu Asp Thr Ser Gly Met Ala Val Tyr Asn Val Thr
            100                 105                 110

Pro His Lys Val Gly Lys Tyr Phe Asn Lys Val Ala Cys Phe Cys Phe
        115                 120                 125

Thr Lys Gln Thr Leu Tyr Pro His Gln Lys Thr Ile Met Pro Val Ser
    130                 135                 140

Phe Phe Ile Asp Pro Ala Ile Glu Thr Asp Pro Glu Thr Ala Asp Val
145                 150                 155                 160

Lys Leu Ile Thr Leu Ser Tyr Val Phe Phe Lys Tyr Lys Glu
                165                 170

<210> SEQ ID NO 4
<211> LENGTH: 1314
<212> TYPE: DNA
<213> ORGANISM: Ehrlichia canis
<220> FEATURE:
<221> NAME/KEY: CDS
<222> LOCATION: (1)..(1314)
<223> OTHER INFORMATION: Protein translated from nucleotides 939 through
      2,252 (ProA).

<400> SEQUENCE: 4 atg atg aaa ttt ttt act tgt ttt ttc ata gtt ttc tta aca ata gcc    48
Met Met Lys Phe Phe Thr Cys Phe Phe Ile Val Phe Leu Thr Ile Ala
1               5                   10                  15 aat cat gct tta tcc ttt aac att aaa gtt aca cat gaa aaa tta gat    96
Asn His Ala Leu Ser Phe Asn Ile Lys Val Thr His Glu Lys Leu Asp
            20                  25                  30
```

```
aat gga atg gaa gta tac gtg att cca aat cat cgc gca cca gca gtc    144
Asn Gly Met Glu Val Tyr Val Ile Pro Asn His Arg Ala Pro Ala Val
         35                  40                  45 atg cac atg gta tta tac aaa gtc ggt gga act gat gat cca gta gga    192
Met His Met Val Leu Tyr Lys Val Gly Gly Thr Asp Asp Pro Val Gly
     50                  55                  60 tac tct gga tta gca cat ttt ttt gaa cac tta atg ttt agt gga aca    240
Tyr Ser Gly Leu Ala His Phe Phe Glu His Leu Met Phe Ser Gly Thr
65                  70                  75                  80 gaa aaa ttt cct aat ctc atc agc aca ctt agt aat ata ggc gga aat    288
Glu Lys Phe Pro Asn Leu Ile Ser Thr Leu Ser Asn Ile Gly Gly Asn
                 85                  90                  95 ttc aat gca agc aca tct caa ttt tgt act ata tac tac gaa tta ata    336
Phe Asn Ala Ser Thr Ser Gln Phe Cys Thr Ile Tyr Tyr Glu Leu Ile
             100                 105                 110 cca aaa caa tat tta tct ctt gca atg gat att gaa tca gac aga atg    384
Pro Lys Gln Tyr Leu Ser Leu Ala Met Asp Ile Glu Ser Asp Arg Met
         115                 120                 125 cag aat ttt aag gtt acc gac aaa gca tta ata aga gaa caa aag gta    432
Gln Asn Phe Lys Val Thr Asp Lys Ala Leu Ile Arg Glu Gln Lys Val
130                 135                 140 gtc tta gaa gaa aga aaa atg aga gtt gaa agc caa gca aaa aac ata    480
Val Leu Glu Glu Arg Lys Met Arg Val Glu Ser Gln Ala Lys Asn Ile
145                 150                 155                 160 cta gaa gaa gaa atg gaa aat gca ttt tat tac aat gga tat ggc aga    528
Leu Glu Glu Glu Met Glu Asn Ala Phe Tyr Tyr Asn Gly Tyr Gly Arg
                 165                 170                 175 cca gta gta gga tgg gaa cat gaa att agc aac tac aac aaa gaa gtt    576
Pro Val Val Gly Trp Glu His Glu Ile Ser Asn Tyr Asn Lys Glu Val
             180                 185                 190 gct gaa gcc ttt cat aag cta cat tat agt cct aat aat gct ata tta    624
Ala Glu Ala Phe His Lys Leu His Tyr Ser Pro Asn Asn Ala Ile Leu
         195                 200                 205 att gta act gga gat gca gat cca caa gaa gta atc aca ctt gca aaa    672
Ile Val Thr Gly Asp Ala Asp Pro Gln Glu Val Ile Thr Leu Ala Lys
     210                 215                 220 caa tac tat ggg aaa ata cca tct aat aat aag aaa cct tca agt caa    720
Gln Tyr Tyr Gly Lys Ile Pro Ser Asn Asn Lys Lys Pro Ser Ser Gln
225                 230                 235                 240 gtt agg gta gaa cca ccg cat aaa aca aat atg act tta aca tta aaa    768
Val Arg Val Glu Pro Pro His Lys Thr Asn Met Thr Leu Thr Leu Lys
                 245                 250                 255 gac agt tca gta gaa atc cca gaa ctg ttt tta atg tat caa ata cca    816
Asp Ser Ser Val Glu Ile Pro Glu Leu Phe Leu Met Tyr Gln Ile Pro
             260                 265                 270 aat ggt att acc aat aaa aac tac ata ctt aac atg atg tta gca gaa    864
Asn Gly Ile Thr Asn Lys Asn Tyr Ile Leu Asn Met Met Leu Ala Glu
         275                 280                 285 ata ctc ggt agt ggt aaa ttc agc ctg ctt tac aat gat ttg gta att    912
Ile Leu Gly Ser Gly Lys Phe Ser Leu Leu Tyr Asn Asp Leu Val Ile
     290                 295                 300 aac aat cca ata gtt aca tcg ata aaa aca gat tat aat tac tta act    960
Asn Asn Pro Ile Val Thr Ser Ile Lys Thr Asp Tyr Asn Tyr Leu Thr
305                 310                 315                 320 gac agc gat aat tac ctt tcc att gaa gct ata cct aaa aac ggg atc   1008
Asp Ser Asp Asn Tyr Leu Ser Ile Glu Ala Ile Pro Lys Asn Gly Ile
                 325                 330                 335 tct aca gaa gct gta gaa caa gaa att cat aaa tgt ata aat aat tat   1056
Ser Thr Glu Ala Val Glu Gln Glu Ile His Lys Cys Ile Asn Asn Tyr
             340                 345                 350
```

-continued

```
tta gaa aat gga att tca gca gaa tat tta gaa agt gca aag tat aaa    1104
Leu Glu Asn Gly Ile Ser Ala Glu Tyr Leu Glu Ser Ala Lys Tyr Lys
        355                 360                 365 gta aaa gca cat tta act tat gca ttt gac gga cta act ttc ata tca    1152
Val Lys Ala His Leu Thr Tyr Ala Phe Asp Gly Leu Thr Phe Ile Ser
370                 375                 380 tat ttt tat ggc atg cat cta ata cta gga gta ccg cta tca gaa atc    1200
Tyr Phe Tyr Gly Met His Leu Ile Leu Gly Val Pro Leu Ser Glu Ile
385                 390                 395                 400 agt aat att tac gat acc ata gac aaa gta agt atc caa gat gtt aac    1248
Ser Asn Ile Tyr Asp Thr Ile Asp Lys Val Ser Ile Gln Asp Val Asn
                405                 410                 415 tcc gct atg gaa aat atc ttt caa aac aat ata aga tta acc ggg cat    1296
Ser Ala Met Glu Asn Ile Phe Gln Asn Asn Ile Arg Leu Thr Gly His
            420                 425                 430 tta tta cct aat gga gaa                                            1314
Leu Leu Pro Asn Gly Glu
        435
```

<210> SEQ ID NO 5
<211> LENGTH: 438
<212> TYPE: PRT
<213> ORGANISM: Ehrlichia canis

<400> SEQUENCE: 5

```
Met Met Lys Phe Phe Thr Cys Phe Phe Ile Val Phe Leu Thr Ile Ala
1               5                   10                  15

Asn His Ala Leu Ser Phe Asn Ile Lys Val Thr His Glu Lys Leu Asp
            20                  25                  30

Asn Gly Met Glu Val Tyr Val Ile Pro Asn His Arg Ala Pro Ala Val
        35                  40                  45

Met His Met Val Leu Tyr Lys Val Gly Gly Thr Asp Asp Pro Val Gly
    50                  55                  60

Tyr Ser Gly Leu Ala His Phe Phe Glu His Leu Met Phe Ser Gly Thr
65                  70                  75                  80

Glu Lys Phe Pro Asn Leu Ile Ser Thr Leu Ser Asn Ile Gly Gly Asn
                85                  90                  95

Phe Asn Ala Ser Thr Ser Gln Phe Cys Thr Ile Tyr Tyr Glu Leu Ile
            100                 105                 110

Pro Lys Gln Tyr Leu Ser Leu Ala Met Asp Ile Glu Ser Asp Arg Met
        115                 120                 125

Gln Asn Phe Lys Val Thr Asp Lys Ala Leu Ile Arg Glu Gln Lys Val
    130                 135                 140

Val Leu Glu Glu Arg Lys Met Arg Val Glu Ser Gln Ala Lys Asn Ile
145                 150                 155                 160

Leu Glu Glu Glu Met Glu Asn Ala Phe Tyr Tyr Asn Gly Tyr Gly Arg
                165                 170                 175

Pro Val Val Gly Trp Glu His Glu Ile Ser Asn Tyr Asn Lys Glu Val
            180                 185                 190

Ala Glu Ala Phe His Lys Leu His Tyr Ser Pro Asn Asn Ala Ile Leu
        195                 200                 205

Ile Val Thr Gly Asp Ala Asp Pro Gln Glu Val Ile Thr Leu Ala Lys
    210                 215                 220

Gln Tyr Tyr Gly Lys Ile Pro Ser Asn Asn Lys Lys Pro Ser Ser Gln
225                 230                 235                 240

Val Arg Val Glu Pro Pro His Lys Thr Asn Met Thr Leu Thr Leu Lys
                245                 250                 255
```

Asp Ser Ser Val Glu Ile Pro Glu Leu Phe Leu Met Tyr Gln Ile Pro
            260                 265                 270

Asn Gly Ile Thr Asn Lys Asn Tyr Ile Leu Asn Met Met Leu Ala Glu
        275                 280                 285

Ile Leu Gly Ser Gly Lys Phe Ser Leu Leu Tyr Asn Asp Leu Val Ile
    290                 295                 300

Asn Asn Pro Ile Val Thr Ser Ile Lys Thr Asp Tyr Asn Tyr Leu Thr
305                 310                 315                 320

Asp Ser Asp Asn Tyr Leu Ser Ile Glu Ala Ile Pro Lys Asn Gly Ile
                325                 330                 335

Ser Thr Glu Ala Val Glu Gln Glu Ile His Lys Cys Ile Asn Asn Tyr
            340                 345                 350

Leu Glu Asn Gly Ile Ser Ala Glu Tyr Leu Glu Ser Ala Lys Tyr Lys
        355                 360                 365

Val Lys Ala His Leu Thr Tyr Ala Phe Asp Gly Leu Thr Phe Ile Ser
    370                 375                 380

Tyr Phe Tyr Gly Met His Leu Ile Leu Gly Val Pro Leu Ser Glu Ile
385                 390                 395                 400

Ser Asn Ile Tyr Asp Thr Ile Asp Lys Val Ser Ile Gln Asp Val Asn
                405                 410                 415

Ser Ala Met Glu Asn Ile Phe Gln Asn Asn Ile Arg Leu Thr Gly His
            420                 425                 430

Leu Leu Pro Asn Gly Glu
        435

<210> SEQ ID NO 6
<211> LENGTH: 1353
<212> TYPE: DNA
<213> ORGANISM: Ehrlichia canis
<220> FEATURE:
<221> NAME/KEY: CDS
<222> LOCATION: (1)..(1353)
<223> OTHER INFORMATION: Protein translated from nucleotides 2,258
      through 3,610 (ProB).

<400> SEQUENCE: 6 atg aga aac ata ttg tgt tac aca tta ata ttg att ttc ttt tca ttc      48
Met Arg Asn Ile Leu Cys Tyr Thr Leu Ile Leu Ile Phe Phe Ser Phe
1               5                   10                  15 aat aca tat gca aat gat ctc aat att aac ata aaa gaa gct aca act      96
Asn Thr Tyr Ala Asn Asp Leu Asn Ile Asn Ile Lys Glu Ala Thr Thr
            20                  25                  30 aaa aat aaa ata cac tat cta tat gtt gaa cat cat aac cta cca aca     144
Lys Asn Lys Ile His Tyr Leu Tyr Val Glu His His Asn Leu Pro Thr
        35                  40                  45 att tcc tta aaa ttt gca ttc aag aaa gca gga tac gct tat gat gcc     192
Ile Ser Leu Lys Phe Ala Phe Lys Lys Ala Gly Tyr Ala Tyr Asp Ala
    50                  55                  60 ttt gat aag caa gga ctt gca tac ttt aca tca aaa ata tta aac gaa     240
Phe Asp Lys Gln Gly Leu Ala Tyr Phe Thr Ser Lys Ile Leu Asn Glu
65                  70                  75                  80 gga tca aaa aac aac tat gct ctc agt ttt gca caa caa tta gaa ggc     288
Gly Ser Lys Asn Asn Tyr Ala Leu Ser Phe Ala Gln Gln Leu Glu Gly
                85                  90                  95 aaa ggt ata gac tta aaa ttt gat ata gac cta gac aat ttt tat ata     336
Lys Gly Ile Asp Leu Lys Phe Asp Ile Asp Leu Asp Asn Phe Tyr Ile
            100                 105                 110 tca tta aaa acc tta tca gaa aac ttt gaa gaa gcc cta gtt tta ctc     384
Ser Leu Lys Thr Leu Ser Glu Asn Phe Glu Glu Ala Leu Val Leu Leu

```
                       115                     120                          125
agt gat tgc ata ttc aac acc gtc aca gat caa gaa ata ttc aat aga        432
Ser Asp Cys Ile Phe Asn Thr Val Thr Asp Gln Glu Ile Phe Asn Arg
    130                     135                     140 ata ata gca gaa cag att gca cat gtt aaa tca tta tat tct gct cct        480
Ile Ile Ala Glu Gln Ile Ala His Val Lys Ser Leu Tyr Ser Ala Pro
145                     150                     155                 160 gaa ttt ata gct aca aca gaa atg aat cac gct ata ttc aaa ggg cac        528
Glu Phe Ile Ala Thr Thr Glu Met Asn His Ala Ile Phe Lys Gly His
                165                     170                     175 cca tat tct aac aaa gtt tac ggg aca tta aat aca atc aat aat atc        576
Pro Tyr Ser Asn Lys Val Tyr Gly Thr Leu Asn Thr Ile Asn Asn Ile
            180                     185                     190 aac cag gaa gac gtt gca tta tat ata aaa aat agt ttt gac aag gaa        624
Asn Gln Glu Asp Val Ala Leu Tyr Ile Lys Asn Ser Phe Asp Lys Glu
        195                     200                     205 caa atc gtt atc agc gca gca gga gat gta gat cca aca cag cta tca        672
Gln Ile Val Ile Ser Ala Ala Gly Asp Val Asp Pro Thr Gln Leu Ser
    210                     215                     220 aat tta cta gat aaa tat att ctt tcc aaa ttg cca tct ggt aat aac        720
Asn Leu Leu Asp Lys Tyr Ile Leu Ser Lys Leu Pro Ser Gly Asn Asn
225                     230                     235                 240 aaa aat acc ata cca gat acg act gtt aat aga gaa gac aca tta tta        768
Lys Asn Thr Ile Pro Asp Thr Thr Val Asn Arg Glu Asp Thr Leu Leu
                245                     250                     255 tat gta cag aga gat gta cca caa agt gtc ata atg ttt gct aca gac        816
Tyr Val Gln Arg Asp Val Pro Gln Ser Val Ile Met Phe Ala Thr Asp
            260                     265                     270 aca gta cca tat cac agc aaa gac tat cat gca tca aac ttg ttc aat        864
Thr Val Pro Tyr His Ser Lys Asp Tyr His Ala Ser Asn Leu Phe Asn
        275                     280                     285 act atg cta ggc gga tta agt ctc aat tca ata tta atg ata gaa tta        912
Thr Met Leu Gly Gly Leu Ser Leu Asn Ser Ile Leu Met Ile Glu Leu
    290                     295                     300 aga gac aag tta gga tta aca tac cat agt agc agt tca cta tct aac        960
Arg Asp Lys Leu Gly Leu Thr Tyr His Ser Ser Ser Leu Ser Asn
305                     310                     315                 320 atg aat cat agt aat gtg cta ttt ggt aca ata ttc act gat aat acc       1008
Met Asn His Ser Asn Val Leu Phe Gly Thr Ile Phe Thr Asp Asn Thr
                325                     330                     335 aca gta aca aaa tgt ata tcc gtc tta aca gat att ata gag cac att       1056
Thr Val Thr Lys Cys Ile Ser Val Leu Thr Asp Ile Ile Glu His Ile
            340                     345                     350 aaa aag tat gga gtt gat gaa gac act ttt gca att gca aaa tct agt       1104
Lys Lys Tyr Gly Val Asp Glu Asp Thr Phe Ala Ile Ala Lys Ser Ser
        355                     360                     365 att acc aac tct ttt att tta tct atg tta aat aac aat aat gtt agt       1152
Ile Thr Asn Ser Phe Ile Leu Ser Met Leu Asn Asn Asn Asn Val Ser
    370                     375                     380 gag ata ttg tta agc tta caa tta cac gat cta gat ccg agt tat att       1200
Glu Ile Leu Leu Ser Leu Gln Leu His Asp Leu Asp Pro Ser Tyr Ile
385                     390                     395                 400 aat aaa tac aat tct tac tac aaa gca ata aca ata gaa gaa gta aat       1248
Asn Lys Tyr Asn Ser Tyr Tyr Lys Ala Ile Thr Ile Glu Glu Val Asn
                405                     410                     415 aaa att gcc aag aaa att tta tct aat gaa tta gta ata att gaa gta       1296
Lys Ile Ala Lys Lys Ile Leu Ser Asn Glu Leu Val Ile Ile Glu Val
            420                     425                     430 gga aaa aac aat aac ata aat ggc aaa caa ata gat gct aaa aaa cac       1344
Gly Lys Asn Asn Asn Ile Asn Gly Lys Gln Ile Asp Ala Lys Lys His
```

```
                    435             440             445
ata ctt ggt                                                         1353
Ile Leu Gly
    450

<210> SEQ ID NO 7
<211> LENGTH: 451
<212> TYPE: PRT
<213> ORGANISM: Ehrlichia canis

<400> SEQUENCE: 7

Met Arg Asn Ile Leu Cys Tyr Thr Leu Ile Leu Ile Phe Phe Ser Phe
1               5                   10                  15

Asn Thr Tyr Ala Asn Asp Leu Asn Ile Asn Ile Lys Glu Ala Thr Thr
            20                  25                  30

Lys Asn Lys Ile His Tyr Leu Tyr Val Glu His His Asn Leu Pro Thr
        35                  40                  45

Ile Ser Leu Lys Phe Ala Phe Lys Lys Ala Gly Tyr Ala Tyr Asp Ala
    50                  55                  60

Phe Asp Lys Gln Gly Leu Ala Tyr Phe Thr Ser Lys Ile Leu Asn Glu
65                  70                  75                  80

Gly Ser Lys Asn Asn Tyr Ala Leu Ser Phe Ala Gln Gln Leu Glu Gly
                85                  90                  95

Lys Gly Ile Asp Leu Lys Phe Asp Ile Asp Leu Asp Asn Phe Tyr Ile
            100                 105                 110

Ser Leu Lys Thr Leu Ser Glu Asn Phe Glu Glu Ala Leu Val Leu Leu
        115                 120                 125

Ser Asp Cys Ile Phe Asn Thr Val Thr Asp Gln Glu Ile Phe Asn Arg
    130                 135                 140

Ile Ile Ala Glu Gln Ile Ala His Val Lys Ser Leu Tyr Ser Ala Pro
145                 150                 155                 160

Glu Phe Ile Ala Thr Thr Glu Met Asn His Ala Ile Phe Lys Gly His
                165                 170                 175

Pro Tyr Ser Asn Lys Val Tyr Gly Thr Leu Asn Thr Ile Asn Asn Ile
            180                 185                 190

Asn Gln Glu Asp Val Ala Leu Tyr Ile Lys Asn Ser Phe Asp Lys Glu
        195                 200                 205

Gln Ile Val Ile Ser Ala Ala Gly Asp Val Asp Pro Thr Gln Leu Ser
    210                 215                 220

Asn Leu Leu Asp Lys Tyr Ile Leu Ser Lys Leu Pro Ser Gly Asn Asn
225                 230                 235                 240

Lys Asn Thr Ile Pro Asp Thr Thr Val Asn Arg Glu Asp Thr Leu Leu
                245                 250                 255

Tyr Val Gln Arg Asp Val Pro Gln Ser Val Ile Met Phe Ala Thr Asp
            260                 265                 270

Thr Val Pro Tyr His Ser Lys Asp Tyr His Ala Ser Asn Leu Phe Asn
        275                 280                 285

Thr Met Leu Gly Gly Leu Ser Leu Asn Ser Ile Leu Met Ile Glu Leu
    290                 295                 300

Arg Asp Lys Leu Gly Leu Thr Tyr His Ser Ser Ser Leu Ser Asn
305                 310                 315                 320

Met Asn His Ser Asn Val Leu Phe Gly Thr Ile Phe Thr Asp Asn Thr
                325                 330                 335

Thr Val Thr Lys Cys Ile Ser Val Leu Thr Asp Ile Ile Glu His Ile
            340                 345                 350
```

```
            Lys Lys Tyr Gly Val Asp Glu Asp Thr Phe Ala Ile Ala Lys Ser Ser
                        355                 360                 365

Ile Thr Asn Ser Phe Ile Leu Ser Met Leu Asn Asn Asn Val Ser
                370                 375                 380

Glu Ile Leu Leu Ser Leu Gln Leu His Asp Leu Asp Pro Ser Tyr Ile
            385                 390                 395                 400

Asn Lys Tyr Asn Ser Tyr Tyr Lys Ala Ile Thr Ile Glu Glu Val Asn
                            405                 410                 415

Lys Ile Ala Lys Lys Ile Leu Ser Asn Glu Leu Val Ile Ile Glu Val
                        420                 425                 430

Gly Lys Asn Asn Asn Ile Asn Gly Lys Gln Ile Asp Ala Lys Lys His
                        435                 440                 445

Ile Leu Gly
                450

<210> SEQ ID NO 8
<211> LENGTH: 663
<212> TYPE: DNA
<213> ORGANISM: Ehrlichia canis
<220> FEATURE:
<221> NAME/KEY: CDS
<222> LOCATION: (1)..(663)
<223> OTHER INFORMATION: Protein translated from nucleotides 4,132
      through 4,794 (mmpA).

<400> SEQUENCE: 8 atg aaa gct cat agc aca agt ata cgg aac ttt cag cct tta gaa aga        48
Met Lys Ala His Ser Thr Ser Ile Arg Asn Phe Gln Pro Leu Glu Arg
1               5                   10                  15 gct gct ata atc att gca gtg tta ggt tta gct gca ttc ttg ttt gct        96
Ala Ala Ile Ile Ile Ala Val Leu Gly Leu Ala Ala Phe Leu Phe Ala
                20                  25                  30 gct gct gcc tgc agt gat cgt ttc caa aga ttg caa tta aca aat cca       144
Ala Ala Ala Cys Ser Asp Arg Phe Gln Arg Leu Gln Leu Thr Asn Pro
            35                  40                  45 ttt gta ata gca gga atg gtt ggc ctt gca gtt ctt tta gtt gct tcc       192
Phe Val Ile Ala Gly Met Val Gly Leu Ala Val Leu Leu Val Ala Ser
        50                  55                  60 tta aca gca gca tta agt ata tgc tta act aaa agt aag caa gtc aca       240
Leu Thr Ala Ala Leu Ser Ile Cys Leu Thr Lys Ser Lys Gln Val Thr
65                  70                  75                  80 caa cat gct att aga cat cgc ttt gga tac gag tca agc act tct tct       288
Gln His Ala Ile Arg His Arg Phe Gly Tyr Glu Ser Ser Thr Ser Ser
                85                  90                  95 tct gta ctg ctt gca ata tca ata att tct tta tta ctt gct gca gca       336
Ser Val Leu Leu Ala Ile Ser Ile Ile Ser Leu Leu Leu Ala Ala Ala
                100                 105                 110 ttt tgt gga aag ata atg ggt aat gac aac cca gat cta ttc ttt agc       384
Phe Cys Gly Lys Ile Met Gly Asn Asp Asn Pro Asp Leu Phe Phe Ser
            115                 120                 125 aag atg caa gaa ctc tcc aat cca ctt gtt gtt gca gct att gta gcc       432
Lys Met Gln Glu Leu Ser Asn Pro Leu Val Val Ala Ala Ile Val Ala
        130                 135                 140 gtt tct gtt ttc cta ctc tca ttc gta atg tat gct gca aag aac att       480
Val Ser Val Phe Leu Leu Ser Phe Val Met Tyr Ala Ala Lys Asn Ile
145                 150                 155                 160 ata agt cca gat aaa caa act cac gtt att ata tta tct aat caa caa       528
Ile Ser Pro Asp Lys Gln Thr His Val Ile Ile Leu Ser Asn Gln Gln
                165                 170                 175 act ata gaa gaa gca aaa gta gat caa gga atg aat att ttg tca gca       576
Thr Ile Glu Glu Ala Lys Val Asp Gln Gly Met Asn Ile Leu Ser Ala
```

```
                        180                 185                 190
gta ctc cca gca gct ggc att gac atc atg act ata gct tct tgt gac      624
Val Leu Pro Ala Ala Gly Ile Asp Ile Met Thr Ile Ala Ser Cys Asp
        195                 200                 205 att tta gca gtg agc agc cgg gga tcc tct cag cat caa                  663
Ile Leu Ala Val Ser Ser Arg Gly Ser Ser Gln His Gln
        210                 215                 220

<210> SEQ ID NO 9
<211> LENGTH: 221
<212> TYPE: PRT
<213> ORGANISM: Ehrlichia canis

<400> SEQUENCE: 9

Met Lys Ala His Ser Thr Ser Ile Arg Asn Phe Gln Pro Leu Glu Arg
1               5                   10                  15

Ala Ala Ile Ile Ile Ala Val Leu Gly Leu Ala Ala Phe Leu Phe Ala
            20                  25                  30

Ala Ala Ala Cys Ser Asp Arg Phe Gln Arg Leu Gln Leu Thr Asn Pro
        35                  40                  45

Phe Val Ile Ala Gly Met Val Gly Leu Ala Val Leu Leu Val Ala Ser
    50                  55                  60

Leu Thr Ala Ala Leu Ser Ile Cys Leu Thr Lys Ser Lys Gln Val Thr
65                  70                  75                  80

Gln His Ala Ile Arg His Arg Phe Gly Tyr Glu Ser Thr Ser Ser
                85                  90                  95

Ser Val Leu Leu Ala Ile Ser Ile Ile Ser Leu Leu Ala Ala Ala
            100                 105                 110

Phe Cys Gly Lys Ile Met Gly Asn Asp Asn Pro Asp Leu Phe Phe Ser
        115                 120                 125

Lys Met Gln Glu Leu Ser Asn Pro Leu Val Val Ala Ala Ile Val Ala
    130                 135                 140

Val Ser Val Phe Leu Leu Ser Phe Val Met Tyr Ala Ala Lys Asn Ile
145                 150                 155                 160

Ile Ser Pro Asp Lys Gln Thr His Val Ile Ile Leu Ser Asn Gln Gln
                165                 170                 175

Thr Ile Glu Glu Ala Lys Val Asp Gln Gly Met Asn Ile Leu Ser Ala
            180                 185                 190

Val Leu Pro Ala Ala Gly Ile Asp Ile Met Thr Ile Ala Ser Cys Asp
        195                 200                 205

Ile Leu Ala Val Ser Ser Arg Gly Ser Ser Gln His Gln
    210                 215                 220

<210> SEQ ID NO 10
<211> LENGTH: 417
<212> TYPE: DNA
<213> ORGANISM: Ehrlichia canis
<220> FEATURE:
<221> NAME/KEY: CDS
<222> LOCATION: (1)..(417)
<223> OTHER INFORMATION: Protein translated from complementary sequence
      derived from nucleotides 4,883 through 5,299 (partial lipoprotein
      signal peptidase homolog).

<400> SEQUENCE: 10 gat cag gta agt aaa tgg tat gta gta aat ttg ata gga gat aaa ggt      48
Asp Gln Val Ser Lys Trp Tyr Val Val Asn Leu Ile Gly Asp Lys Gly
1               5                   10                  15 gta ata gag ata tta agc ttc ttg cgc ttt act aca gtg tgg aat cct      96
Val Ile Glu Ile Leu Ser Phe Leu Arg Phe Thr Thr Val Trp Asn Pro
```

```
                20                  25                  30
gga att agt ttt ggt ata tta aat aac ttt gaa tat agt aat gtt gtt    144
Gly Ile Ser Phe Gly Ile Leu Asn Asn Phe Glu Tyr Ser Asn Val Val
         35                  40                  45 ttt tgt agt atc tcg att ttg att act tgt gtt tta tgc tac tta ttt    192
Phe Cys Ser Ile Ser Ile Leu Ile Thr Cys Val Leu Cys Tyr Leu Phe
 50                  55                  60 ata gta cag cca cat tat aga tta cct ctt gta atc att att ggg ggg    240
Ile Val Gln Pro His Tyr Arg Leu Pro Leu Val Ile Ile Ile Gly Gly
 65                  70                  75                  80 tca ata gga aat atc ata gat aga ata aga tat ggt gct gtc tat gat    288
Ser Ile Gly Asn Ile Ile Asp Arg Ile Arg Tyr Gly Ala Val Tyr Asp
                 85                  90                  95 ttt ata gat ttt tat atc aat aac tta cat tgg cct gta ttc aac ctg    336
Phe Ile Asp Phe Tyr Ile Asn Asn Leu His Trp Pro Val Phe Asn Leu
            100                 105                 110 gcg gat tct ttt ata ttt tta ggt ata gta ata ata atg gca aag agt    384
Ala Asp Ser Phe Ile Phe Leu Gly Ile Val Ile Ile Met Ala Lys Ser
        115                 120                 125 aat aac cac atg aaa caa att aac tgt aac tcc                        417
Asn Asn His Met Lys Gln Ile Asn Cys Asn Ser
    130                 135

<210> SEQ ID NO 11
<211> LENGTH: 139
<212> TYPE: PRT
<213> ORGANISM: Ehrlichia canis

<400> SEQUENCE: 11

Asp Gln Val Ser Lys Trp Tyr Val Val Asn Leu Ile Gly Asp Lys Gly
1               5                   10                  15

Val Ile Glu Ile Leu Ser Phe Leu Arg Phe Thr Thr Val Trp Asn Pro
            20                  25                  30

Gly Ile Ser Phe Gly Ile Leu Asn Asn Phe Glu Tyr Ser Asn Val Val
        35                  40                  45

Phe Cys Ser Ile Ser Ile Leu Ile Thr Cys Val Leu Cys Tyr Leu Phe
    50                  55                  60

Ile Val Gln Pro His Tyr Arg Leu Pro Leu Val Ile Ile Ile Gly Gly
65                  70                  75                  80

Ser Ile Gly Asn Ile Ile Asp Arg Ile Arg Tyr Gly Ala Val Tyr Asp
                85                  90                  95

Phe Ile Asp Phe Tyr Ile Asn Asn Leu His Trp Pro Val Phe Asn Leu
            100                 105                 110

Ala Asp Ser Phe Ile Phe Leu Gly Ile Val Ile Ile Met Ala Lys Ser
        115                 120                 125

Asn Asn His Met Lys Gln Ile Asn Cys Asn Ser
    130                 135

<210> SEQ ID NO 12
<211> LENGTH: 41
<212> TYPE: DNA
<213> ORGANISM: Artificial
<220> FEATURE:
<223> OTHER INFORMATION: oligonucleotide

<400> SEQUENCE: 12
aggcttgttc agggtgaaga agaatccaac gacaaaagct t                      41

<210> SEQ ID NO 13
<211> LENGTH: 41
```

```
<212> TYPE: DNA
<213> ORGANISM: Artificial
<220> FEATURE:
<223> OTHER INFORMATION: oligonucleotide

<400> SEQUENCE: 13
aagcttttgt cgttggattc ttcttcaccc tgaacttgcc a                              41

<210> SEQ ID NO 14
<211> LENGTH: 9
<212> TYPE: PRT
<213> ORGANISM: Artificial
<220> FEATURE:
<223> OTHER INFORMATION: Nonapeptide sequence VQGEESNDK from IL-1beta

<400> SEQUENCE: 14

Val Gln Gly Glu Glu Ser Asn Asp Lys
1               5
```